US012636405B2

(12) United States Patent
Planck et al.

(10) Patent No.: US 12,636,405 B2
(45) Date of Patent: May 26, 2026

(54) RESORBABLE COVERING MEMBRANE FOR MEDICAL WOUND AREA TREATMENT

(71) Applicant: PolyMedics Innovations GmbH, Denkendorf (DE)

(72) Inventors: Heinrich Planck, Nuertingen (DE); Erhard Mueller, Stuttgart (DE); Svenja Reimer, Aichtal (DE); Christian Planck, Kirchheim (DE); Helmut Hierlemann, Goeppingen (DE)

(73) Assignee: PolyMedics Innovations GmbH, Denkendorf (DE)

( * ) Notice: Subject to any disclaimer, the term of this patent is extended or adjusted under 35 U.S.C. 154(b) by 235 days.

(21) Appl. No.: 18/327,838

(22) Filed: Jun. 1, 2023

(65) Prior Publication Data

US 2023/0390453 A1 Dec. 7, 2023

Related U.S. Application Data

(63) Continuation of application No. PCT/EP2021/084215, filed on Dec. 3, 2021.

(30) Foreign Application Priority Data

Dec. 3, 2020 (DE) ..................... 10 2020 215 295.0

(51) Int. Cl.
*A61F 13/00* (2024.01)
*A61L 26/00* (2006.01)

(52) U.S. Cl.
CPC ......... *A61L 26/009* (2013.01); *A61L 26/0052* (2013.01); *A61L 26/0095* (2013.01)

(58) Field of Classification Search
None
See application file for complete search history.

(56) References Cited

U.S. PATENT DOCUMENTS 6,706,058 B2 * 3/2004 Hierlemann .......... A61L 26/009
528/359
8,735,644 B2 * 5/2014 Johnson .............. A61F 13/0203
604/289

(Continued)

FOREIGN PATENT DOCUMENTS

CN 108770341 A * 11/2018 ........... A61L 27/025
DE 102007000574 A1 * 4/2009 ........... A61L 15/225

(Continued)

OTHER PUBLICATIONS

CN 108770341 A translation (Year: 2018).*

(Continued)

*Primary Examiner* — Kim M Lewis
(74) *Attorney, Agent, or Firm* — Orbit IP, LLP; Marc G. Martino

(57) ABSTRACT

A covering membrane for medical wound area treatment is disclosed for burns or for preventing adhesion. The covering membrane has a substrate layer including a polymer material as well as collagen particles which have a particle size I of more than 80 μm and are disposed in such a way as to be fixedly embedded in at least some portions of the polymer material of the substrate layer. The covering membrane further relates to a process for manufacturing such a covering membrane.

22 Claims, 4 Drawing Sheets

(56)                    References Cited

U.S. PATENT DOCUMENTS

| 8,951,598 | B2 | | 2/2015 | Chang et al. | |
|---|---|---|---|---|---|
| 9,131,713 | B2 | | 9/2015 | Dick et al. | |
| 9,162,006 | B2 | * | 10/2015 | Hoefinghoff | ............ A61L 15/32 |
| 9,839,722 | B2 | * | 12/2017 | McKay | ................. A61L 27/365 |
| 11,110,208 | B2 | | 9/2021 | Koenig | |

FOREIGN PATENT DOCUMENTS

| DE | 10 2008 036 576 A1 | 2/2010 | |
|---|---|---|---|
| DE | 10 2016 214 258 A1 | 2/2018 | |
| EP | 0 170 979 A2 | 2/1986 | |
| EP | 1 181 941 A2 | 2/2002 | |
| EP | 2 428 233 A1 | 3/2012 | |
| EP | 2 997 077 A1 | 3/2016 | |
| JP | 4716570 B2 * | 7/2011 | ............. A61L 17/12 |
| WO | 2014/183770 A1 | 11/2014 | |

OTHER PUBLICATIONS

DE 10200700574 A1 translation (Year: 2009).*
EP 1182941 B1 (Year: 2006).*
Chen et ai. "The Use of a Novel PLGA Fiber/Collagen Composite Web as a Scaffold for Engineering of Articular cartilage Tissue with Adjustable Thickness", Journal for Biomedical Material Research, 2003, 1170-1180. (Year: 2003).*
JP 4716570 B2 Translation (Year: 2011).*

* cited by examiner

RESORBABLE COVERING MEMBRANE FOR MEDICAL WOUND AREA TREATMENT

CROSS-REFERENCE TO RELATED APPLICATIONS

This continuation application claims priority to PCT/EP2021/084215 filed on Dec. 3, 2021 which has published as WO 2022/117840 A2 and also the German application number 10 2020 215 295.0 filed on Dec. 3, 2020, the entire contents of which are fully incorporated herein with these references.

DESCRIPTION

Field of the Invention

The present invention relates to a resorbable covering membrane for medical wound treatment.

Background of the Invention

Such a covering membrane is known, for example, from EP 1 181 941 A2 and marketed by PolyMedics Innovations GmbH, Germany, under the name Suprathel®. In medical practice, the covering membrane is established as a wound contact material, e.g., as a skin substitute material in burn wounds or also for the treatment of what is known as degloving, i.e., of avulsion wounds of the skin.

U.S. Pat. No. 8,951,598 B2 discloses a covering membrane which comprises a biodegradable polymer substrate layer made of polylactic acid or polyglycolic acid which is doped with collagen nanoparticles. The polymer substrate layer can comprise, for example, a polylactide-glycolipid copolymer (PLGA) having 10 to 40 wt % (i.e., weight percent) nanoscale collagen particles.

Although the covering membrane mentioned at the outset offers pain-relieving and anti-infectious effects in the open wound area treatment and permits a largely undisturbed formation of granulation tissue with at the same time good mechanical properties, the hemostatic effect of the covering membranes is quite limited and the covering membrane exhibits only a slow adsorption and absorption capacity of the fluids on wound surfaces that are bloody or wetted with exudate. It is known that post-operative adhesions frequently occur in clinical practice after surgery in the abdominal cavity. Such tissue adhesions can result in recurrent chronic pain, infertility and possibly even mechanical small intestine closure (=ileus). It is known that microscopically small peritoneal tissue lesions can cause adhesions in conjunction with blood. In this respect, supplementary prophylaxis measures are useful, which favor an accelerated post-operative healing and counteract such adhesions. Due to their slow adsorption and absorption capacity of liquids, the aforementioned covering membranes are therefore also suitable only to a limited extent for intraperitoneal use for the purpose of preventing adhesion.

It is therefore the object of the invention to specify a covering membrane which has improved hemostatic properties and allows an even broader application spectrum. Furthermore, it is the object of the invention to provide a process for manufacturing such a covering membrane.

SUMMARY OF THE INVENTION

The object relating to the covering membrane is achieved according to the invention by a covering membrane having the features specified in an independent claim. The manufacturing process according to the invention is specified in other claims. Preferred developments of the invention are specified in the dependent claims and in the description.

According to the invention, the covering membrane has collagen particles having a particle size of more than 80 μm, which are fixedly embedded in at least some portions of the polymer material of the substrate layer. Due to the known swelling capacity of fibrillar collagen, i.e., collagen which is intact in its secondary or tertiary structure, the binding of water to the covering membrane can be accelerated and the water binding capacity of the covering membrane per unit area can be increased. Fibrillar or structurally intact collagen is understood in the present application to mean collagen whose α- and β bands are detectable in the SDS-PAGE test.

Due to the fact that the collagen particles are anchored in the—in turn water-absorbent—polymer material of the substrate layer, the water absorption can also be promoted by the polymer material of the substrate layer itself. In the case of wound area application of the covering membrane, excess blood plasma and/or wound exudate can thus be removed more quickly and more effectively from the wound area. The swelling of the collagen particles increases the thickness of the covering membrane, at least locally, so that the distance between the covering membrane and the wound tissue treated therewith can increase, at least in a locally limited manner.

In addition, rapid contact with blood present on the wound area, or wound exudate, by the collagen particles can be made possible. It is known that, in the case of wound contact of collagen, the binding of the von Willebrand factor (VWF) to the collagen and to the corresponding receptor of the thrombocyte membrane of thrombocytes and the adhesion of thrombocytes is promoted. The emptying of thrombocyte granules (degranulation) can be enhanced and the plasmatic blood clotting (secondary hemostasis) can be triggered or amplified. This is advantageous for an accelerated and effective hemostasis and does not exist when nanoscale collagen particles are used. As a result of the particularly high degree of bioavailability of the collagen, the hemostatic properties of the covering membrane can thus be improved, and also a vascularization of the wound area and thus wound healing can be accelerated.

In the case of a correspondingly flexibly deformable design of the covering membrane, this can be adapted in a simple manner, even to intraperitoneal surfaces which are difficult to cover in three dimensions, and to wound areas of the skin, for example in the region of joints.

The collagen particles preferably have a particle size in the range from 80 μm to 500 μm, particularly preferably in the range from 100 μm to 250 μm, very particularly preferably in the range from 100 μm to 150 μm. It has surprisingly been found in practice that the hemostatic effect of the collagen in situ decreases beyond an average particle size of approximately 500 μm, and the anchoring of the collagen in the substrate layer is no longer sufficiently stable compared to the mechanical forces acting during the handling and application of the covering membrane. This can result in undesired shearing of the collagen particles from the substrate layer. In this case of the particle size between 100 μm to 150 μm, a particularly reliable hemostasis can be achieved.

According to a preferred development of the invention, the covering membrane comprises 0.4 to 80 wt %, preferably 0.5 to 25 wt %, collagen particles. It should be noted that the improved hemostatic properties of the sheet material provided by the collagen are already achieved at approximately 1 wt % collagen. In this respect, the sheet material can comprise, in particular, 0.4-2 wt % collagen particles.

According to a preferred development of the invention, at least some of the collagen particles extend away from the substrate layer. The collagen particles thus form a collagen pole on the rear or front side of the substrate layer. The size of the collagen particles alone makes the covering membrane more hydrophilic in the region of the collagen pole than without such collagen pole. In this design of the covering membrane, a direct bioavailability of the collagen particles and thus an even more rapid hemostatic effect of the covering membrane can be achieved.

Alternatively or additionally, at least some of the collagen particles can bulge over the front or rear surface region of the substrate layer encompassing or surrounding the respective collagen particle. In this case, the respective collagen particle is preferably completely fixedly embedded in the polymer material of the substrate layer.

According to the invention, the aforementioned collagen pole of the substrate layer has a structure height of more than 10%, preferably of more than 20%, of a nominal thickness of the substrate layer. As a result, a reliable contacting of the wound by the collagen particles can be achieved in a simplified manner, independently of the smallest possible bending radius of the covering membrane. This is advantageous for the liquid-absorbing and hemostatic effect of the covering membrane over its entire functional surface. In this way, the formation of unwanted blood or wound fluid accumulations on the wound and also an associated risk of infection can be counteracted particularly reliably.

According to the invention, the substrate layer can have a collagen pole of collagen fibers on both sides. This eliminates the risk of an inverted application of the covering membrane on the wound area to be treated therewith. Furthermore, the collagen poles of the two sides of the substrate layer can differ from one another in their nominal thickness, the average density of their collagen fibers per unit area of the covering membrane, and/or the size of their collagen particles. As a result, the same covering membrane can be used for different requirements of wound management, and thus their scope of application can be further expanded. In addition, an undesired adhesion of covering membrane portions to one another can thus be counteracted when covering membrane portions are folded over.

The collagen pole of one side of the covering membrane can comprise, for example, collagen particles having an average particle size of 100 to 150 μm, and the pole of the other side of the covering membrane collagen particles can have an average particle size of between 250 and 500 μm. As a result, the swelling behavior of the collagen particles of the respective trim or pole of the substrate layer can be correspondingly adapted to the wound region to be treated.

The collagen particles of the covering membrane can be produced in particular from native type I and/or type III collagen, in particular bovine collagen. Such collagen is available on the market in sufficient amounts and in high purity.

According to the invention, the substrate layer can comprise, in particular, a copolymer based on the monomers lactide, glycolide, trimetalcarbonate, ε-caprolactone and/or 1,4-dioxan-2-one or polyhydroxybutyrate (PHB) or mixtures of these polymers. As a result, the covering membrane can develop an anti-infectious and pain-reducing effect, the complete hydrolytic and enzymatic degradability being completely maintained.

According to the invention, the substrate layer can comprise 20 wt % to 99.6 wt % copolymer and/or polyhydroxybutyrate, and 0.4 wt % to 80 wt % collagen particles having a particle size >80 μm, preferably 0.8 wt % to 25 wt % of the collagen particles.

According to the invention, the substrate layer can in particular comprise a terpolymer of 65 to 87 wt % lactide, 5 to 20 wt % trimethylene carbonate and 5 to 20 wt % E-caprolactone. In the terpolymer, the monomers lactide, trimethylene carbonate and ε-caprolactone can be present in particular in the range from 85/10/5 to 70/20/10 wt %.

The substrate layer of the covering membrane preferably has a nominal thickness d of 50 to 3000 μm, preferably of 80 to 500 μm or of 800 to 2500 μm.

The process according to the invention for manufacturing the covering membrane explains above comprises the following steps: comminuting provided and preferably dried native collagen into collagen particles having an average particle size greater than 80 μm, preferably greater than 100 μm; producing a polymer solution of a resorbable polymer and an appropriate solvent; a) suspending the collagen particles in the polymer solution and applying the collagen suspension thus obtained, having the collagen particles suspended therein, on a flat substrate; or b) applying the polymer solution to a flat substrate after previous sprinkling of the substrate with the collagen particles and/or after subsequent sprinkling of the polymer solution with the collagen particles; and removing the solvent by drying, in particular by freeze-drying.

The suspension/dispersion of the collagen particles in the polymer solution must take place very carefully in order not to further damage the collagen particles directly or by shear forces, in particular to comminute them further. Very finely distributed collagen (<50 μm) may degrade very quickly in the polymer solution to gelatin, so that the fibrils of the collagen particles having their original helix shape are destroyed. It is therefore necessary, in terms of the process, to maintain the particle size of more than 80 μm in order to maintain the integrity and desired function of the collagen in vivo. The focus should therefore be on a large-scale and structure-preserving suspension/dispersion of the collagen particles. According to the invention, this is preferably achieved by dispersing or suspending the collagen particles in the polymer solution by stirring for a maximum of two minutes, preferably for a maximum of one minute.

It is also possible to suspend/disperse the collagen particles by stirring for a maximum of two minutes, preferably one minute, in the pure solvent and subsequent careful mixing of the collagen suspension with the polymer solution.

The substrate layer of the covering membrane stabilizes by means of the drying. Length segments of the collagen particles arranged outside the substrate layer can emerge in part from the flat substrate during drying or during detachment of the covering membrane. If the flat substrate is designed, for example, in the form of a plate, in particular a glass plate, having a completely planar surface, then the rear side of the dried covering membrane is correspondingly designed so as to be smooth, i.e., in particular without collagen particles extending away from the rear side of the substrate material. If the covering membrane is to have a collagen pole on both sides, then a glass plate comprising micro-depressions or alternatively a substrate having a microporous coating can be used as a flat substrate.

If the collagen particles are scattered on the substrate or on the polymer solution/collagen suspension applied to the substrate, this can be carried out solely by gravity or also in a forced manner, by means of a compressed gas/compressed air. In this way, the collagen particles can be anchored particularly reliably in the polymer solution or the collagen suspension.

According to the invention, the native collagen is preferably dried before its comminution, or the comminuted collagen particles are preferably dried before being suspended in the solution. In the first case, particularly efficient comminution of the collagen, and in the latter case a particularly efficient suspension of the collagen particles in the solution, can be achieved.

Further advantages of the invention can be found in the description and the drawings. Likewise, according to the invention, the aforementioned features and those which are to be explained below can each be used individually or together in any desired combinations. The embodiments described below are not to be understood as an exhaustive list, but rather have an exemplary character for illustrating the invention.

DETAILED DESCRIPTION OF THE
PREFERRED EMBODIMENTS

Figure 1:
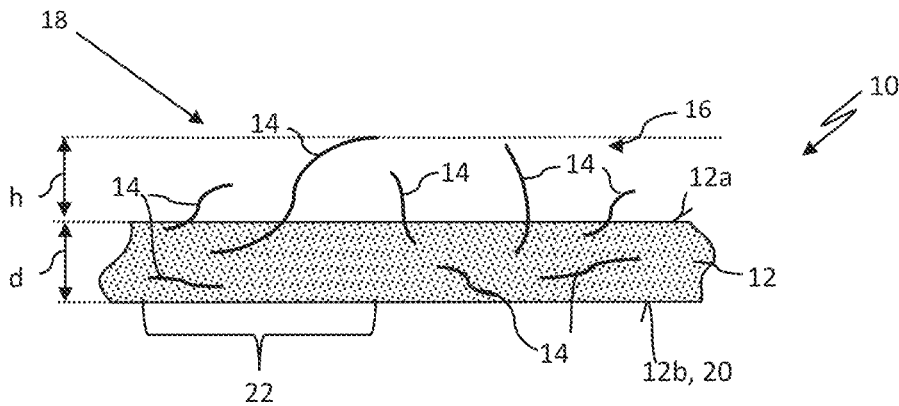
FIG. 1 is a schematic sectional view of a covering membrane having a substrate layer in which collagen particles having a particle size of greater than 80 μm are anchored.

FIG. 1 shows a covering membrane 10 for medical wound area treatment, which is also suitable in particular for intraperitoneal adhesion prevention. The covering membrane 10 comprises a substrate layer 12 having a front and a rear side 12a, 12b. The substrate layer 12 is formed here structurally by a copolymer based on the monomers lactide, trimethylene carbonate, e-caprolactone and/or 1,4-dioxan-2-one, or polyhydroxybutyrate (PHB) or mixtures of these polymers. The substrate layer 12 is therefore biocompatible and degradable and completely resorbable hydrolytically and/or by the body's own enzymes.

The substrate layer has a nominal thickness d which can be from 50 to 3000 μm, preferably from 80 to 500 μm, or from 1000 to 2500 μm, depending on the mechanical application requirements placed on the covering membrane 10.

For improved hemostasis or faster absorption of blood and wound fluid, collagen particles 14 are fixedly embedded in at least some portions of the material of the substrate layer 12. In other words, the collagen particles 14 are anchored in the material of the substrate layer 12. The collagen particles 14 can be fixedly embedded in their entirety in the polymer material of the substrate layer and, according to FIG. 1, extend away from the substrate layer 12, or bulge over the front side, at least in part, as explained further below in connection with FIG. 4. If the collagen particles 14 extend away from the substrate layer, they can together form a collagen pole 16 of the substrate layer 12. In the ready-to-use state of the covering membrane 10, the structure height h of the collagen pole 16 can be more than 10%, preferably more than 20%, of the nominal thickness d of the substrate layer 12.

The collagen particles 14 all consist of comminuted native collagen, for example Type I and/or Type III collagen, and can, in particular, be of bovine, murine or porcine origin. The collagen particles 14 have a particle size I of more than 80 μm, preferably between 100 μm and 500 μm, particularly preferably between 100 μm and 250 μm.

In the embodiment shown in FIG. 1, due to the collagen pole 16 the covering membrane 10 has two different wear faces 18, 20. If the covering membrane 10 is applied with its pole-side wear face 18 to a wound area (not shown), a direct contacting of the wound area by the collagen particles 14 is made possible. In this way, a particularly high bioavailability of the collagen is ensured and its functional advantages in wound area treatment are exhausted at an early stage and comprehensively. These include, in particular, the known hemostatic properties of fibrillar collagen, the swelling capacity of which is due to a pronounced absorption capacity of blood and wound exudate, and the favorable effects thereof with respect to rapid vascularization of the wound area and wound healing. In practice, it has been shown that even low mass fractions of the collagen particles 14 favor the aforementioned effects. In this respect, the covering membrane 10 can comprise between 0.5 and 80 wt % (i.e., weight percent) collagen particles 14, preferably between 0.8 and 25 wt % collagen particles 14.

In practice, the covering membrane 10 can be folded and respective folding portions (not shown) can be placed on top of each other, e.g., by their mutually facing rear side 12b. This offers the advantage, in particular, in the case of preventing adhesion, of a particularly large fluid absorption capacity based on the surface unit 22 of the folded covering membrane 10 contacting the wound area in each case. In addition, a laparoscopic application of the covering membrane can thereby be facilitated.

According to an embodiment not shown in the drawings, the covering membrane can also have a collagen pole 16 of collagen particles 14 on both sides. This can, in practice, firstly counteract an accidental inverted application of the covering membrane and provide a collagen wear face 20 on both sides. At the same time, in the case of the wound application of the covering membrane, onerous adhesion of the covering membrane 10 to itself can be counteracted. It should be noted that the collagen poles 16 of the front and rear sides 12a, 12b of the substrate layer 12 can differ from one another in the average density of their collagen particles 14 per unit area 22 of the covering membrane 10 and/or the size of their collagen particles 14 or their structure height h. As a result, a covering membrane 10 having different collagen wear faces 18, can be provided, and thus the possible range of use of the covering membrane 10 during wound area treatment can be expanded.

Figure 2:
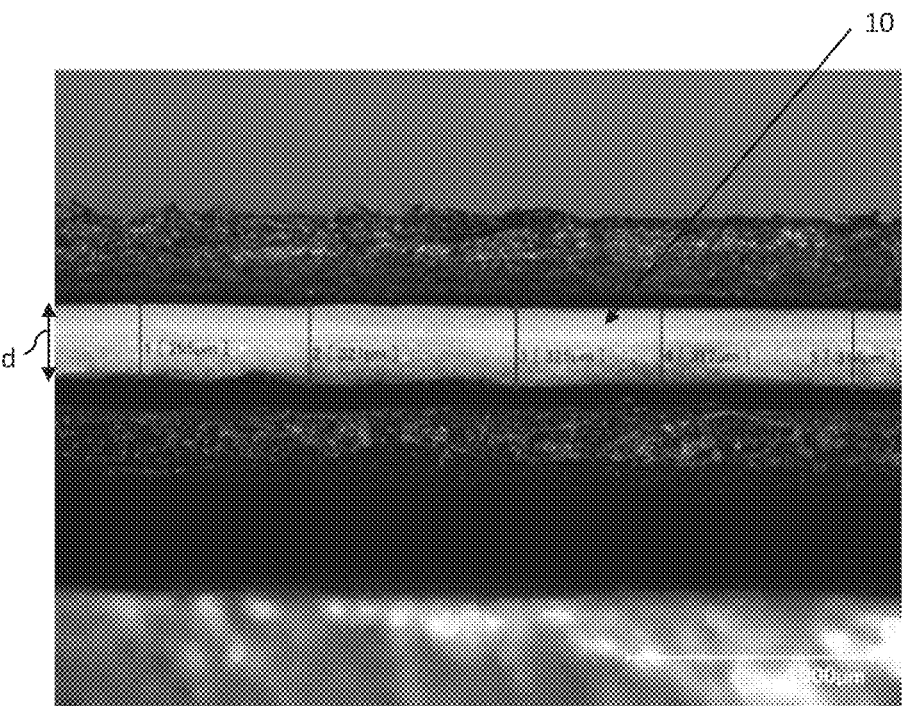
FIG. 2 is a side view of a covering membrane.
Figure 3:
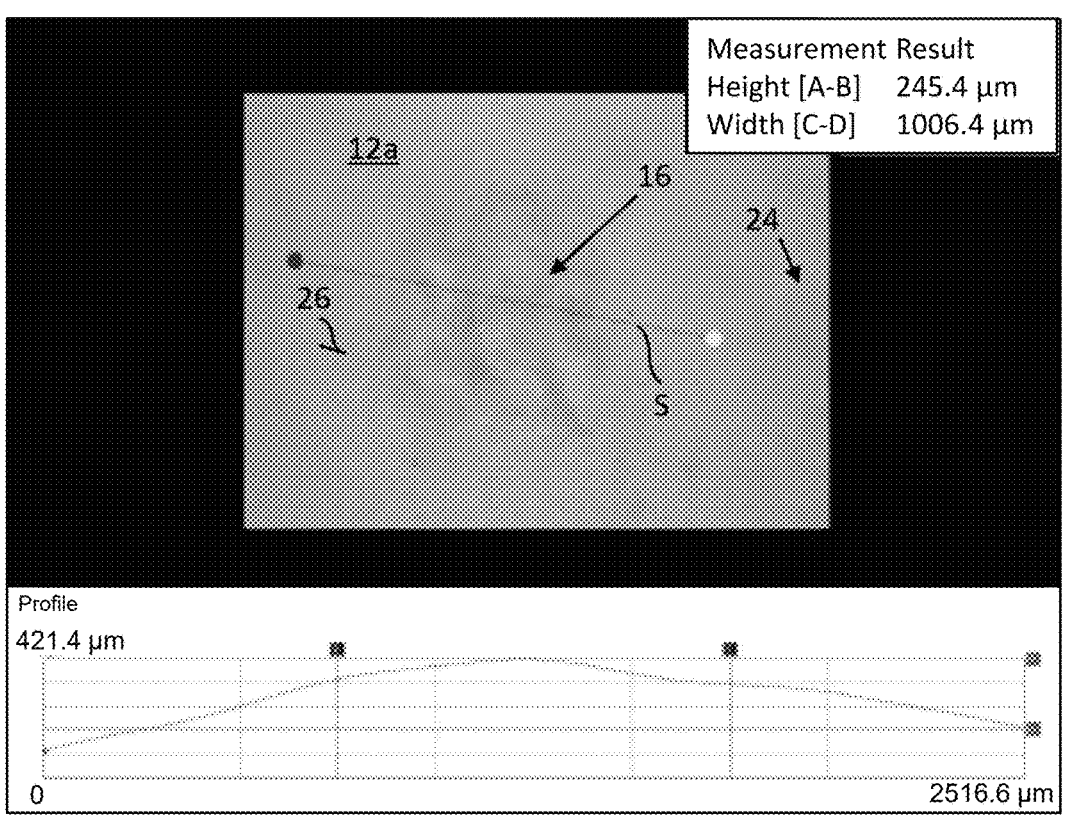
FIG. 3 is a plan view of the covering membrane according to FIG. 2, showing a collagen particle completely fixedly embedded in the polymer material of the substrate layer, which bulges over the (planar) surface region of the substrate layer that surrounds the collagen particle in each case.
Figure 4:
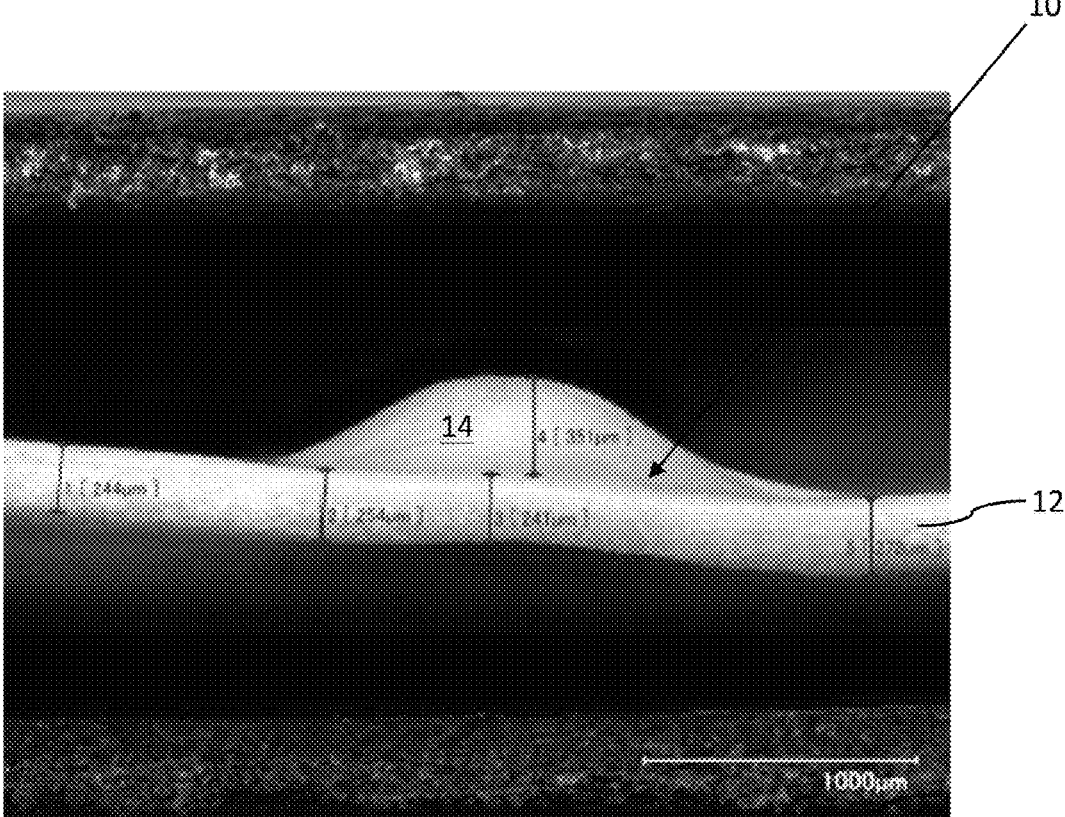
FIG. 4 shows the covering membrane according to FIG. 2 after several hours of swelling in water at 37° Celsius.

FIGS. 2 to 4 show a further covering membrane 10 in its ready-to-use state. This covering membrane differs from the embodiment explained above in connection with FIG. 1 essentially in that the collagen particles 14 are completely fixedly embedded in the polymer material of the substrate layer 12. In other words, in this case the collagen particles 14 are completely surrounded or enveloped by the polymer material of the substrate layer. FIG. 2 shows a side view of the covering membrane, in which the nominal thickness d of the substrate layer can be clearly seen.

FIG. 3 shows the ready-to-use covering membrane 10 in the region of a collagen particle 14 in a microscopic plan view and having a height profile along the measuring section designated S. The collagen particle 14 bulges together with the polymer material (in a locally delimited manner) over the surface region 24 the front face 12a of the substrate layer 12 surrounding the collagen particle 14. In this case, the surface region 24 of the substrate layer 12 is planar or substantially planar.

If the covering membrane 10 shown in FIG. 3 is inserted in water and subsequently investigated by measurement, then increased swelling of the covering membrane 10 compared to collagen-free substrate layer portions of the covering membrane or of the surface region of the substrate layer 12 surrounding the collagen particle 14 is found in the region of a collagen particle 14, i.e., in a locally limited manner. FIG. 4 shows, in this respect, a microscope image of the covering membrane 10 after a water bath at 37° C. for 22 hours. The nominal thickness d (cf. FIG. 1) of the covering membrane 10 is approximately 250 µm on average, according to the height profile image, the collagen particle 14 shown (see FIG. 1) protruding approximately 350 µm beyond the surface region 24 of the substrate layer 12 (collagen particle-free substrate layer portion) encompassing the collagen particle 14.

Water contacting the covering membrane 10 diffuses through the polymer material of the substrate layer that covers the collagen particles 14 and is taken up by the collagen particles 14. The collagen particles 14 thus extract water from a bleeding wound and thus accelerate the hemostasis. The combination of the collagen particles 14 and the synthetic resorbable polymer (e.g., poly-lactide-caprolactone-trimethylene carbonate) combines the positive properties of both materials. The resorbable polymer material of the substrate layer 12 is in direct contact with the wound (e.g., burn wound) and can improve wound healing by enzymatic release of lactic acid and develop a pain-relieving and anti-infections effect.

Figure 5:
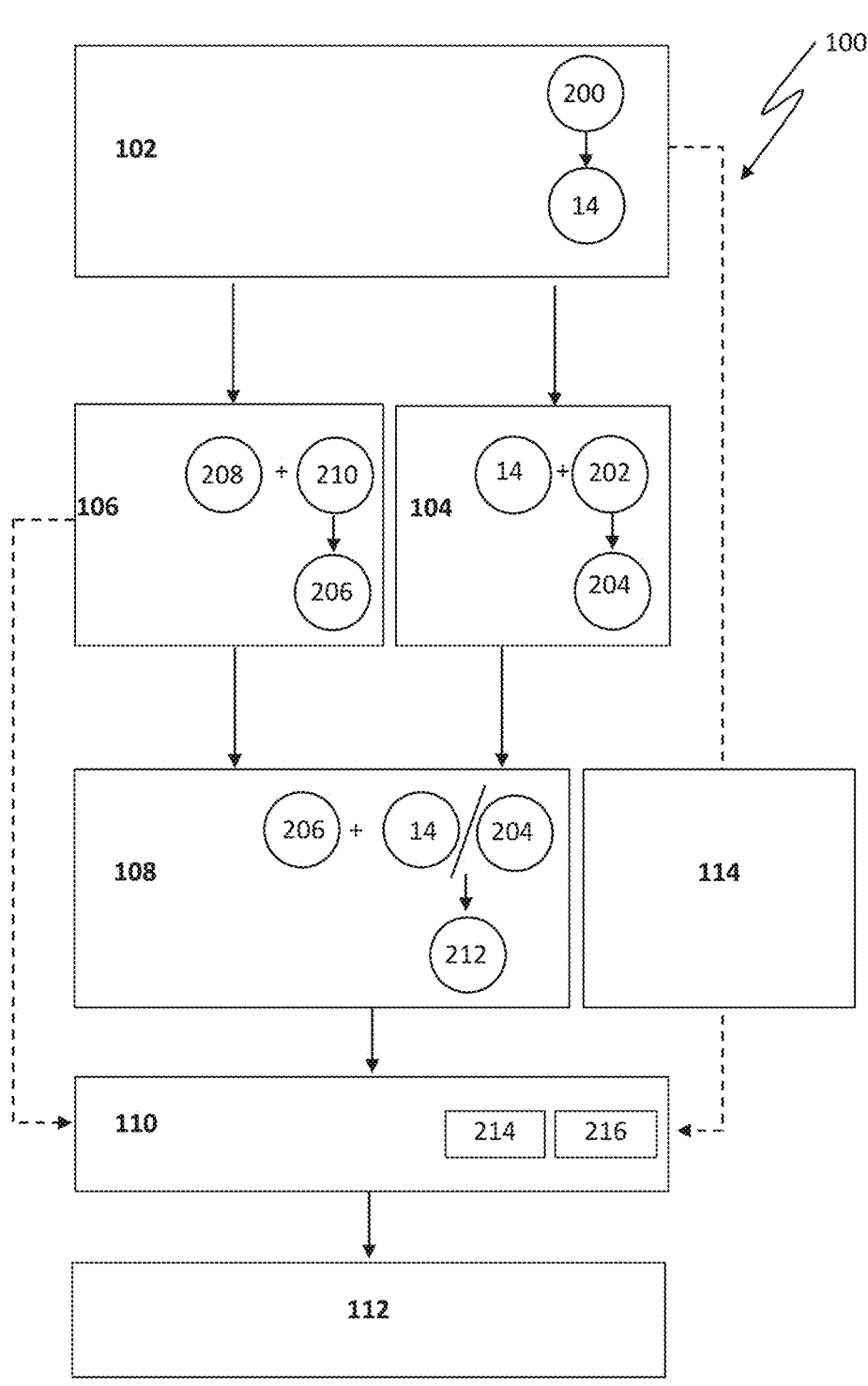
FIG. 5 is a block diagram of a process according to the invention for manufacturing a covering membrane according to the invention.

Manufacturing Process:

In the following embodiments of a process 100 for manufacturing the covering membrane 10 according to the invention, reference is additionally made to the block diagram, with individual process steps of the process 100, shown in FIG. 5.

The process 100 has the following process steps:

In a first step 102, provided and preferably dried native collagen 200 is comminuted to collagen particles 14 having a particle size greater than 80 µm, preferably greater than 100 µm.

The collagen particles 14 can, in a subsequent optional step 104, be suspended in an organic solvent 202, for example dimethyl sulfoxide (DMSO), forming a collagen stock suspension 204. Surprisingly, the collagen particles 14 are stable or largely stable in pure DMSO, such that the collagen particles 14 suspended in DMSO do not degrade.

In a further step 106, a polymer solution 206 is prepared from a resorbable polymer 208 and a suitable solvent 210.

In step 108, the collagen particles 14 or the collagen particles 14 contained in the collagen stock suspension 204 are suspended/dispersed in the polymer solution 206 such that a collagen suspension 212 is obtained.

Here, care must be taken that the size and functionality of the collagen particles 14 (i.e. structural integrity with detectability of α- and β-bands in SDS PAGE test) is/are preserved. Thus, it has surprisingly been found that the collagen particles 14 are, for example, not stable in a solution 206 of a statistical terpolymer of D, L-lactide-trim ethylene carbonate caprolactone and can degrade over time to form collagen particles 14 having a particle size <50 µm. In this respect, on the one hand rapid processing of the collagen suspension 212 is advisable. Furthermore, when the collagen particles 14 are mixed with the polymer solution 206, extremely gentle, in particular temporally limited, stirring is advisable, in order not to further comminute or destroy the collagen particles 14, directly or by shearing. For this purpose, for example a dispersing device of the Ultra Turrax® series from IKA®-Werke GmbH & CO. KG, Germany can be used.

Figure 6:
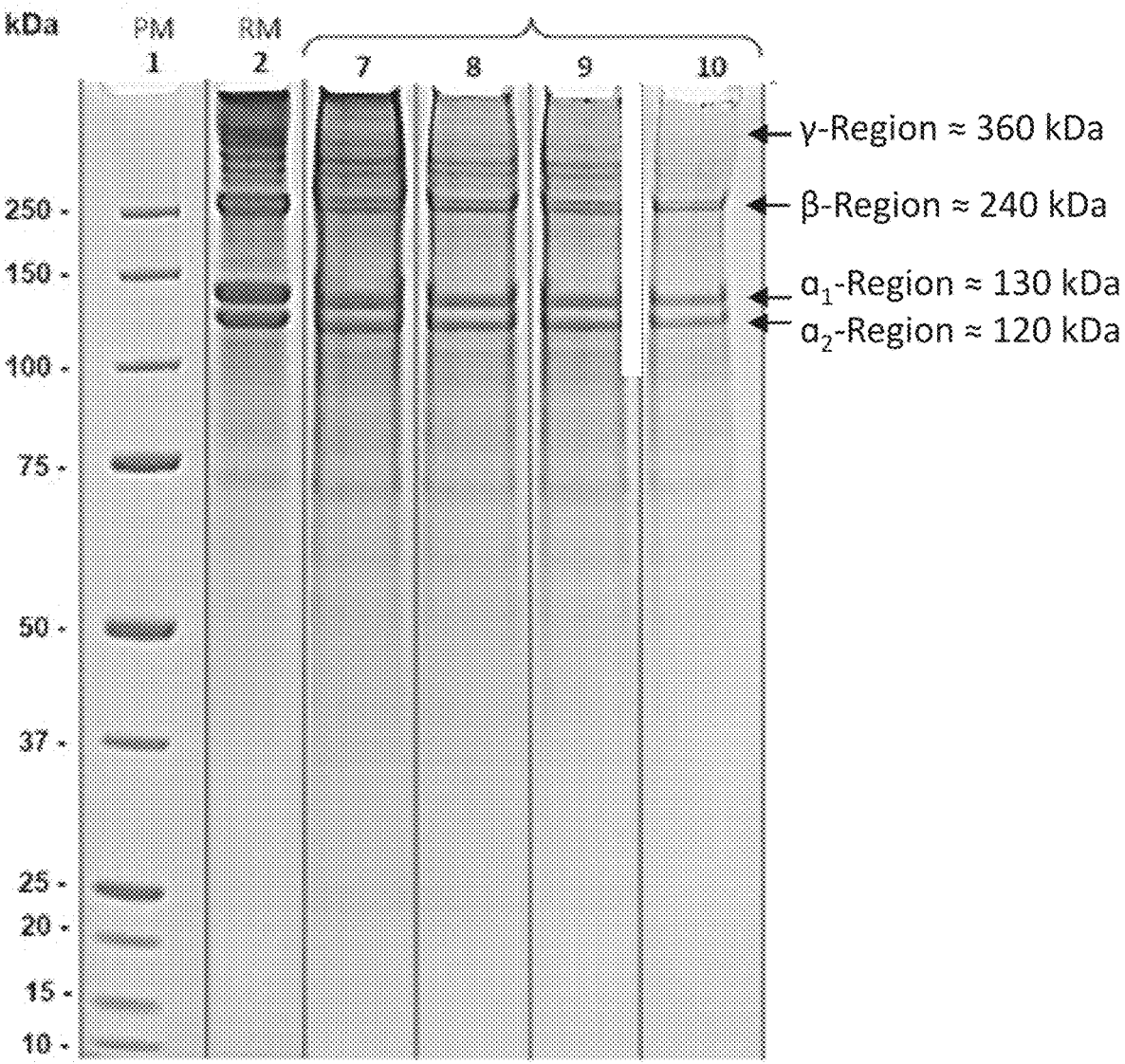
FIG. 6 shows an SDS-PAGE test for detecting an undesired degradation of collagen particles depending on the mixing time when mixing the collagen particles with a polymer solution.

FIG. 6 shows the result of an SDS-PAGE test (sodium dodecyl sulfate polyacrylamide gel electrophoretic test) of the collagen suspension 212, depending on the stirring time by means of an aforementioned Ultra Turrax® stirrer. In the first (left-hand) trace, a protein marker PM (protein marker: "Precision Plus Protein Standard" from BioRad having defined molar weights between 10 and 250 kDa; 10 µl sample volume) was applied. The reference bands typical for the protein marker PM are found. A solution comprising native bovine collagen (sample volume 4 µl) was applied in the second trace. A sample (sample volume 33 µl) of the collagen suspension 212 having a stirring time of 2×15 s (trace 7), 2×30 s (trace 8), 2×60 s (trace 9) and 2×5 min (trace 10) was applied in the trace nos. 7 to 10 in each case.

The collagen bands typical for collagen particles 14 (α, β and γ regions) are clearly visible at an Ultra Turrax® mixing time of 2×15 s (trace 7). The intensity of the bands in the γ- and β region already decreases increasingly at a mixing time of 2×30 s and 2×60 s. In the case of a mixing time of 2×5 min, the bands in the γ region are almost no longer discernible and the bands in the α- and β region are markedly less pronounced. Surprisingly, the reduction of the intensity of the α-, β-, and γ regions thus clearly shows a degradation of the collagen even after stirring for 5 minutes. In the case of even longer stirring, the alpha and beta bands in the collagen suspension 212 are no longer discernible either (not shown). For the above reasons, the collagen particles 14 are preferably dispersed/suspended in the respective polymer solution 206 for less than 2 minutes, very particularly preferably at most 1 minute.

The collagen suspension 212 thus obtained is preferably applied, in step 110, to a flat substrate 216 by means of a doctor blade 214. As a flat substrate 216, in particular a glass plate can be used.

In a final step 112, the collagen suspension 212 is dried, in particular freeze-dried, and the solvent 210 is thereby removed.

Alternatively or in addition to steps 104 and 108, the collagen particles 14 may, in step 114, also be applied or scattered on the flat substrate 210 before application of the solution 206 or the collagen stock suspension 212 to the flat substrate 216, or applied or scattered on the solution 206/collagen suspension 212 after the application of the solution 206/collagen suspension 212 to the flat substrate 210. In the latter case, this can be done by means of a compressed gas or by means of compressed air, in order to introduce the collagen particles 14 into the solution 206 or the collagen suspension 212 at least in portions.

EXAMPLE 1

In step 102, 0.5 g of dried bovine collagen 200 is comminuted to collagen particles 14 having a particle size >80 μm. The collagen particles 14 are subsequently dispersed in step 104 in an organic solvent 202 to obtain a collagen stock suspension 204. For this purpose, the collagen particles 14 are added for example to 49.5 g of dimethyl sulfoxide (DMSO) and dispersed gently therein over 15 sec. This gives a 1 collagen stock suspension 204.

In the subsequent step 106, in this case by way of example 150 g of a 23% solution 206 of a statistical terpolymer of D,L-lactide-trimethylene carbonate caprolactone in a solvent 208 is provided.

Subsequently, in step 108, a total of 50 g of the 1% DMSO-collagen stock suspension 204 is mixed with 150 g of the 23% solution of a statistical terpolymer of D, L-lactide-trimethylene-carbonate-caprolactone to form the collagen suspension 212, and homogenized twice, over 15 sec in each case, by means of stirring.

In step 110, the collagen suspension 212 is spread onto substrate 216, for example a glass plate, using a doctor blade 214 having a doctor blade gap of 250 μm, and then freeze-dried in step 112. This results in a covering membrane 10 of approximately 120 μm nominal thickness d consisting of 98.6% lactide trimethylene carbonate caprolactone terpolymer and 1.4% bovine collagen particles 14.

EXAMPLE 2

In step 108, a total of 1.15 g of ground collagen particles 14 having a particle size >80 μm is added to 100 ml of a 23% polymer solution 206 of a statistical terpolymer of D, L-lactide trimethylene carbonate caprolactone in DMSO, and stirred gently to form the collagen suspension 212.

The collagen suspension 212 is subsequently spread onto the flat substrate 216 in step 110, using a doctor blade 214 having a doctor blade gap of 500 μm. Finally, the solvent 210 is removed from the collagen suspension 212 by freeze-drying the collagen suspension 212. This results in an approximately 100-250 μm thick covering membrane in the form of a collagen composite membrane composed of 95% of a statistical terpolymer consisting of lactide-trimethylene-carbonate-caprolactone and 5% collagen particles 14 having a particle size >80 μm.

EXAMPLE 3

If, according to example 2, a total of 4.6 g collagen particle 14 having a particle size >80 μm is suspended in the polymer solution 206 then, with otherwise unchanged further process steps, an approximately 100-250 μm thick covering membrane 10 consisting of 80% of a statistical terpolymer of D, L-lactide-trimethylene carbonate-caprolactone and 20% bovine collagen particles 14 of a particle size above 80 μm is obtained.

EXAMPLE 4

In the first step 102, native bovine collagen is comminuted to collagen particles 14 having an average particle size >80 μm. Thereafter, in step 104, 0.25 g of the dried collagen particles 14 is added to 49.5 g DMSO and dispersed gently for 15 sec. A 1% collagen stock suspension 204 is obtained in the process. In step 108, 50 g of the 1% DMSO collagen stock suspension 204 are mixed with 150 g of a 12.5% solution of a statistical terpolymer of D, L-lactide-trimethylene-carbonate-caprolactone, and homogenized by stirring for 2×15 sec. The collagen suspension 212 thus obtained is spread onto the flat substrate 216 using a doctor blade 214 having a doctor blade gap of 600 μm.

In step 112, the collagen suspension 212 is freeze-dried, such that a covering membrane of approximately 180 μm nominal thickness d consisting of 98.6% lactide trimethylene carbonate caprolactone terpolymer and 1.4% bovine collagen particles 14 of a particle size >80 μm is obtained.

What is claimed is:

1. A covering membrane configured for medical wound area treatment including for burns or for preventing adhesion, comprising:
   a substrate layer comprising a resorbable polymer material; and
   collagen particles which have an average particle size between 100 μm and 250 μm, where the collagen particles are disposed fixedly embedded in at least some portions of the resorbable polymer material of the substrate layer;
   wherein at least some of the collagen particles bulge over a surface region of the substrate layer surrounding the respective collagen particle or extend away from the substrate layer to form a collagen pole.

2. The covering membrane according to claim 1, wherein the collagen particles have the average particle size in the range between 100 μm and 150 μm.

3. The covering membrane according to claim 1, wherein the covering membrane comprises between 0.4 and 80 weight percent collagen particles.

4. The covering membrane according to claim 1, wherein the covering membrane comprises between 0.4 and 25 weight percent collagen particles.

5. The covering membrane according to claim 1, wherein the covering membrane comprises between 0.4 and 2 weight percent collagen particles.

6. The covering membrane according to claim 1, wherein, in the ready-to-use state of the covering membrane, the collagen pole has a structure height h of more than 10% of a nominal thickness d of the substrate layer.

7. The covering membrane according to claim 1, wherein, in the ready-to-use state of the covering membrane, the collagen pole has a structure height h of more than 20% of a nominal thickness d of the substrate layer.

8. The covering membrane according to claim 1, wherein the substrate layer has the collagen pole on both sides.

9. The covering membrane according to claim 1, wherein the collagen particles are produced from native bovine, type I and/or type III collagen.

10. The covering membrane according to claim 1, wherein the substrate layer comprises: a copolymer based on the monomers lactide, trimethylene carbonate, glycolide, ε-caprolactone and/or 1,4-dioxan-2-one, or polyhydroxybutyrate (PHB); or mixtures of these polymers.

11. The covering membrane according to claim 10, wherein the substrate layer comprises a terpolymer of 65 to 87 weight percent lactide, 5 to 20 weight percent trimethyl carbonate, and 5 to 20 weight percent E-caprolactone.

12. The covering membrane according to claim 11, wherein the monomers lactide, trimethylene carbonate and ε-caprolactone are present in the terpolymer, in the range of 87/8/5 to 70/20/10 weight percent.

13. The covering membrane according to claim 1, wherein the substrate layer has a nominal thickness d of 50 μm to 3000 μm.

14. The covering membrane according to claim 1, wherein the substrate layer has a nominal thickness d of 80 μm to 500 μm.

15. The covering membrane according to claim 1, wherein the substrate layer has a nominal thickness d of 1000 μm to 2500 μm.

16. A process for manufacturing the covering membrane according to claim 1, comprising the steps of:

comminuting provided and dried native collagen to collagen particles having an average particle size between 100 μm and 250 μm;

preparing a polymer solution of a resorbable polymer and a suitable solvent;

a) suspending the collagen particles in the polymer solution and applying the collagen suspension thus obtained, with the collagen particles suspended therein, onto a flat substrate; or b) applying the polymer solution to a planar substrate after previous sprinkling of the substrate with the collagen particles or with subsequent sprinkling of the polymer solution with the collagen particles; and removing the solvent by drying.

17. The process according to claim 16, wherein the step of comminuting provided and dried native collagen to collagen particles having an average particle size is greater than 100 μm.

18. The process according to claim 16, wherein removing the solvent by drying is by freeze-drying.

19. The process according to claim 16, wherein a copolymer based on the monomers lactide, trimetal carbonate, glycolide, ε-caprolactone and/or 1,4-dioxan-2-one or poly-hydroxybutyrate (PHB) or mixtures of these polymers is used.

20. The process according to claim 16, wherein the collagen particles are dispersed in the polymer solution by stirring for a maximum of two minutes.

21. The process according to claim 16, wherein the collagen particles are dispersed in the polymer solution by stirring for a maximum of one minute.

22. The covering membrane according to claim 1, wherein the average particle size is an equivalent spherical diameter, wherein the collagen particles have the equivalent spherical diameter between 100 μm and 250 μm.

* * * * *